United States Patent [19]

Gagescu

[11] Patent Number: 4,830,713
[45] Date of Patent: May 16, 1989

[54] REGENERATION METHOD AND DEVICE

[75] Inventor: Dan Gagescu, Petit-Lancy, Switzerland

[73] Assignee: Orbisphere Laboratories (Inc.), Vèsenaz, Switzerland

[21] Appl. No.: 890,155

[22] Filed: Jul. 28, 1986

[30] Foreign Application Priority Data

Aug. 25, 1985 [EP] European Pat. Off. ......... 85810387

[51] Int. Cl.[4] .......................................... G01N 27/26
[52] U.S. Cl. .................................. 204/1 T; 204/402; 204/415
[58] Field of Search ............... 204/402, 415, 1 T, 418

[56] References Cited

U.S. PATENT DOCUMENTS 3,503,861  3/1970  Volpe .................................. 204/402
4,541,901  9/1985  Parker ................................. 204/402
4,566,949  1/1986  Berger ................................ 204/402

Primary Examiner—John F. Niebling
Assistant Examiner—Ben C. Hsing
Attorney, Agent, or Firm—Werner W. Kleeman

[57] ABSTRACT

A method of regenerating a membrane-enclosed amperometric or Clark cell having an operative current range for electroanalytical operation limited by a maximum current density of typically not more than 100 $\mu A/cm^2$ at the working electrode by subjecting at least one of the probe electrode in contact with a regeneration electrolyte, while the membrane is removed, to a regeneration current for causing a current density in the range of from about 1 to about 1000 $mA/cm^2$ which is substantially higher, e.g. by a factor of at least 10 and preferably at least 100, than the maximum current density in electroanalytical operation.

The device for use in this method comprises an enclosure having a lower end and an upper end; the lower end is sealingly closed by the sensing end of the probe; the device comprises a regenerator electrode external to the probe arranged within the enclosure to provide a space for holding a regeneration electrolyte in contact with the regenerator electrode and the probe electrodes; a lead connects the regenerator electrode with a current source having a second outlet connected with at least one of the probe electrodes.

26 Claims, 1 Drawing Sheet

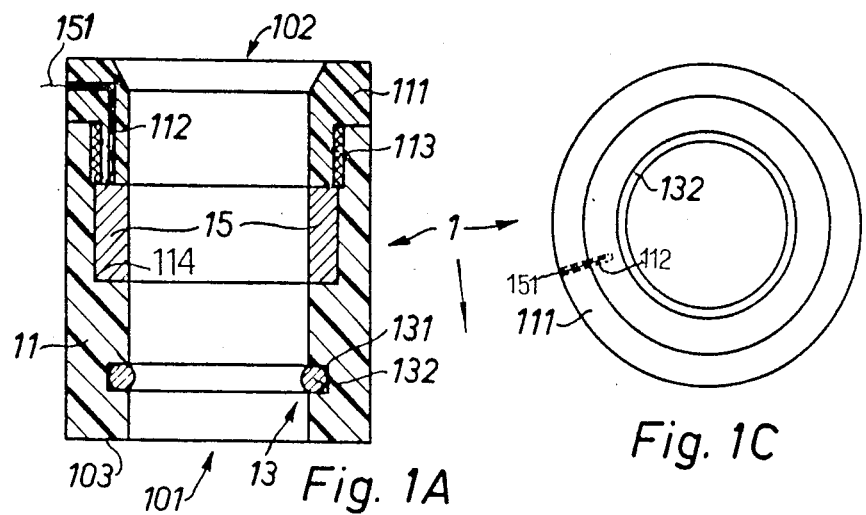
Fig. 1A
Fig. 1C
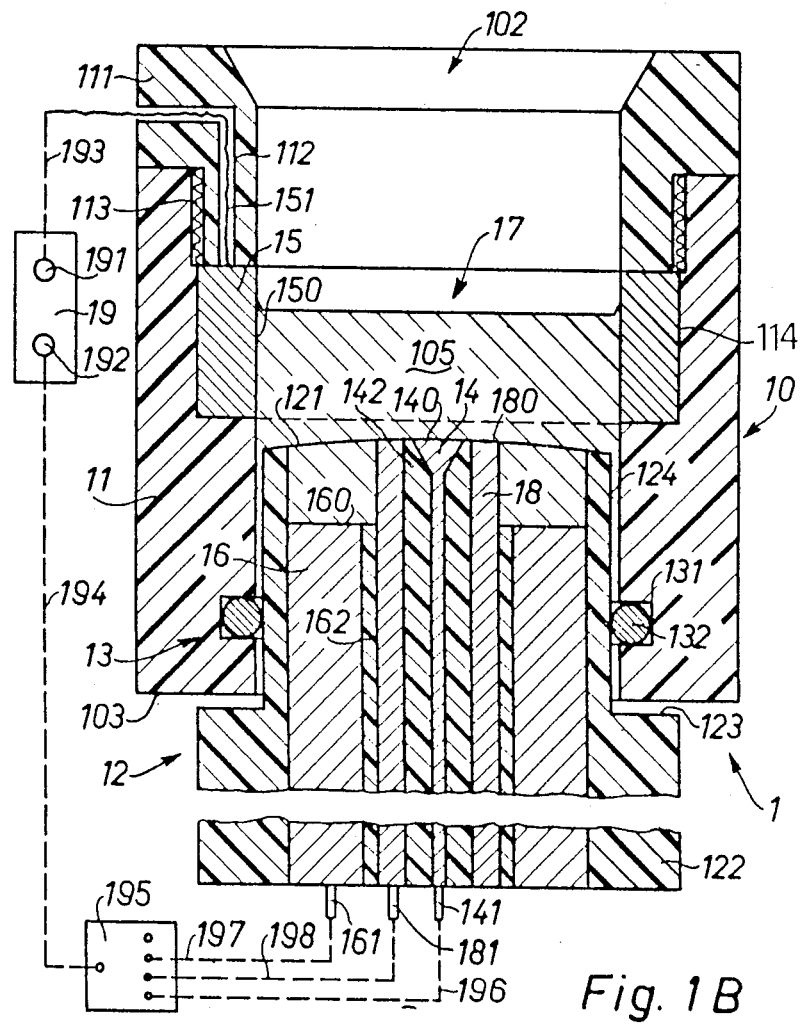
Fig. 1B

REGENERATION METHOD AND DEVICE

CROSS-REFERENCE TO RELATED CASES

This application generally relates to subject matter disclosed in the following U.S. cases:

U.S. application Ser. No. 773,163, filed Mar. 1, 1977, issued as U.S. Pat. No. 4,096,047; U.S. application Ser. No. 164,291, filed June 30, 1980, issued as U.S. Pat. No. 4,325,797; U.S. application Ser. No. 319,708, filed Nov. 9, 1981, issued as U.S. Pat. No. 4,372,021; U.S. application Ser. No. 345,536, filed Feb. 3, 1982, issued as U.S. Pat. No. 4,518,477, U.S. application Ser. No. 493,316, filed May 10, 1983, issued as U.S. Pat. No. 4,563,249; U.S. patent application Ser. No. 743,155, filed June 10, 1985, and U.S. application Ser. No. 821,747, filed Jan. 23, 1986.

BACKGROUND OF THE INVENTION

(a) Field of the Invention

The invention relates, generally, to electroanalysis and, specifically, to regeneration methods and devices for maintaining or even improving certain qualities of the amperometric instruments.

(b) Description of Prior Art

Electroanalytical methods and probes have always been looked at with the expectation that they offer an avenue to quick and effective analysis of constituents or constituent concentrations in ambient media of vital interest, such as water and air; however, it was the advent of the membrane-enclosed amperometric cell, also termed "Clark Cell" because of Leland C. Clark Jr., the inventor of U.S. Pat. No. 2,913,386 (issued 1959), that caused an effective break-through.

Reliability and precision of analysis with the Clark Cell have increased substantially and many new fields of application have become apparent. In fact, there are few fields of technology where detection of critical yet possibly minute concentrations of elemental oxygen and other electroactive species of interest (herein termed EASI) is without importance.

Probably the most important single factor in the success of the Clark Cell or membrane-enclosed amperometric cell (MEAC for short herein) is the membrane assumed to be a "semipermeable" stratum between an ambient or probe medium that contains the species of interest and the electrolyte within the cell; the membrane "protects" the cell's interior.

Many films of organic polymers are substantially impermeable to the cell electrolyte, frequently an aqueous and generally fluid medium capable of generating ions, while permitting passage of gases to a larger or lesser extent, and all such films tend to normally prevent "pollution" of the cell electrolyte and of the electrodes by probe components.

Main exceptions are pollution problems by "electrode poisoning", typically by sulphurous gases, such as $H_2S$ or $SO_2$, and "electrode plating", typically by electrodeposition of metal from the counter electrode on the working electrode.

While various specific methods have been suggested to avoid such pollution through the membrane and within the cell, the most generally accepted method of dealing with these problems is the combined use of electrodes made of, or coated with, noble metals, typically gold, metals from the plantinum group (Ru, Rh, Pd, Os, Ir, Pt) and alloys containing major portions of one or more such noble metals, together with regular maintenance of MEACs by exchanging both the cell electrolyte and the membrane.

Of course, use of noble metals for the electrode and exchanging the electrolyte have other reasons as well but the chemically inert nature of noble metals, notably in a polished, e.g. mirror-bright, state provided for easy control and removal of surface impurities at the electrode surface.

Frequently, poisoning effects, plating and other undesirable electrode changes will be detected because of discoloration, speck formation, or other irregularities that will easily be seen by visual inspection of the surface of the electrode and, at the same time, can be removed easily by simple conventional cleaning techniques, i.e. to wash away or dissolve pollutant deposits on the electrode with a relatively mild chemical reagent, such as ammonia, thiourea, thiosulphate and the like complexing agents and, perhaps, to polish the electrode surface.

Previous research by the patentee has led to the discovery of several "quasi-polluting" effects, such as permeation of electrolyte into the interface between the electrode and an adjacent insulator as well as various permeation-induced or solubility-related but always unwanted contributions to, or changes of, the measuring current; these effects and various structures and methods for avoiding them have been disclosed, for example, in U.S. Pat. Nos. 4,096,047 and 4,518,477, European Patent No. 0 043 611 and U.S. Ser. No. 743,155 filed June 10, 1985.

As a result, MEAC sensitivity has been increased to the extent that trace amounts of typical electroactive species of interest including oxygen and hydrogen in the ppb ($10^{-9}$) range have become detectable and continuously surveyable by routine analysis methods. Increased MEAC sensitivity, while leading to new fields of application, also and inevitably has the side effect of pointing up new problems that could not have been detected with less sensitive methods and which may reside in the particularities of a specific field of application, such as microbial growth problems in biotechnological fields, or in the measuring instrument.

Considering that ppb-measurement with MEACs entails measurement of currents in the Microampere to Picoampere range it will be understood that very minor changes indeed, such as aging of polymers with concurrent change of electrical properties, or long-term creep strength of structural materials may become observable and have an influence upon the measuring method or the measured results, and it is possible that time-dependent "degeneration" of a probe's behaviour will be caused by a variety of effects, some of which may involve small and hardly detectable surface changes induced by sorptive or chemical processes at the electrode surface.

Insofar as such effects are time-related and not easily reversible without exchange of probe components, they can be generally described as "aging" effects of MEACs and similar electroanalytical probes resulting in a limited life of the probe.

Patentee's review of long-term operation behaviour of MEACs has pointed up two specific problem factors that might, at least in part, be considered time-dependent in the sense of increasing with the operation time or operative life of a MEAC and being not, or not easily, reversible; the factors can be summed up by the terms "sluggish response" and "noisy current output" of MEACs.

"Sluggish response" means that the probe response to a predetermined change of EASI concentration becomes slower with continued length of operation and may be determined, for example, by exposing an oxygen-sensing MEAC to normal air, then dipping it into an oxygen-free probe medium, measuring the time interval required to reach a substantially constant "zero-current" and comparing such results in dependence upon the time length of MEAC operation.

"Noisy current output" is observed when a probe is exposed to a probe medium that includes a constant EASI concentration yet generates an uneven signal, again observing time-related changes, if any.

Both "sluggish response" and "noisy current output" have been found to be more or less time-dependent, sometimes to the extent of limiting the useful operative life of a MEAC.

OBJECTS AND SUMMARY OF THE INVENTION

Accordingly, it is an essential object of the present invention to provide a regeneration method for membrane-enclosed amperometric cells and similar electroanalytical probes (EAP hereinafter) with the beneficial effect of eliminating or substantially reducing time-related change of the probe behaviour including, but not restricted to, sluggish response and noisy current output of MEACs and similar EAPs.

Another important object is a device for use in such method.

Further objects will become apparent as the specification proceeds.

The term "regeneration" as used herein is intended to indicate a complete or nearly complete (say at least 75% of an original value) recovery of at least one operational property that has deteriorated as a consequence of a more or less prolonged operation, or an operation causing accelerated deterioration of an operational probe property, said recovery being achieved without replacement of main cell components other than electrolyte and membrane, and substantially without loss of material such as would be incurred as a consequence of grinding or other drastic ways of materially removing a deteriorated electrode surface.

Now, it has been found according to the invention that regeneration in the sense just defined of MEACs and similar EAPs can be achieved if one or more electrodes of the probe is/are subjected, in the presence of a non-polluting and non-aggressive aqueous electrolyte, to the effect of a current density that is substantially and typically 100 to 1000 times higher than the maximum current densities that occur when the probe is used for electroanalytical operation. In order to generate such current densities at a probe electrode for probe regeneration a voltage is applied between that probe electrode and a regenerator electrode which is external to the probe and is in electrolytically conductive contact (=permitting passage of ions) with the probe electrode, normally by also contacting the electrolyte present.

It has been found according to the invention that time-dependent deteriorations of EAPs including sluggish response and noisy current output can be substantially eliminated by such a regeneration method up to the point that the cell will show its best ex-factory or "virgin" properties.

A "non-polluting and non-aggressive aqueous electrolyte" for the inventive method is one which under the operating conditions of the regeneration including temperature, regeneration time, applied current density and voltage will neither attack the probe (e.g. as evidenced by the absence of dissolved electrode material in the electrolyte after regeneration) nor deposit any noxious constituents or products on the electrode surface. Specific and preferred examples will be given below. An electrolyte constituent is regarded as "noxious" herein if its presence causes a deterioration of probe performance.

DISCUSSION OF PREFERRED EMBODIMENTS

Operating conditions of the inventive regeneration process include temperatures in the range from just above the freezing point of the electrolyte to just below its boiling point; a temperature range between 10° and 50° C. is preferred and a range between 15° and 40° C. is particularly preferred. Temperatures below 15° C. are not normally preferred because longer treatment times may be required to achieve a given degree of regeneration (e.g. measured in terms of a defined response time or current "noise"); temperatures above 50° C. are less preferred as they may damage, endanger, or deteriorate one or more cell components. Generally, the temperature during regeneration treatment as measured in the electrolyte should be within the "normal operative temperature range" of the electroanalytical probe (term defined, e.g. in EP No. 0 085 450) that is regenerated according to the invention.

The time normally required for optimum regeneration according to the invention will be in the range of from a few seconds, say 5 seconds, to a few hours, say up to 5 hours; typical preferred times at temperatures between 20° to 30° C. will be in the range of 20 seconds to 200 minutes, when the electrode surface consists of nobel metals and if current densities and voltages are within their preferred ranges as well.

As indicated above, current densities (expressed herein as $\mu A/cm^2$ or $mA/cm^2$) that are operable in the inventive regeneration method must be substantially higher than the maximum current density at which the probe is used for electroanalytical operation. In general, the current density for the inventive regeneration will be at least ten times and, typically, at least a hundred times higher than those of analytical probe operation. For example, typical probes of the MEAC type for determination of oxygen, hydrogen and similar EASI will operate with a working electrode having an electrolyte-exposed surface of gold, platinum-group metal or alloys thereof at current densities at the working electrode (cathode or anode, respectively) of not more and preferably less than 100 $\mu A/cm^2$, e.g. up to 25 $\mu A/cm^2$. Accordingly, the regeneration current density at the working electrode should be above 1 $mA/cm^2$, preferably above 10 $mA/cm^2$ and typically in the range of from 10 to 1000 $mA/cm^2$, a range of from 50 to 800 $mA/cm^2$ being preferred for many purposes. The upper current density limit is not believed to be critical per se as regards regeneration and current densities above 1000 $mA/cm^2$ could be used if the probe structure (e.g. diameter of lead wires, soldered connections, etc.) is capable to absorb the Joulean heat caused by such currents without damage.

For reasons to be explained in more detail below, the voltage applied between a probe's electrode and the external regenerator electrode should generally be above 1.2 V, e.g. in the range of from 1.5 to 15 V; a preferred upper limit of the voltage range is 4.5 V.

Typical electroanalytical probes that can be regenerated according to the invention have at least one working electrode ("sensing electrode") and at least one counter electrode (frequently a "consumable" electrode); the EAP may further have a so-called guard electrode (cf. DE Patent No. 2,851,447) and one or more of these probe electrodes can be involved in the inventive regeneration.

For most purposes, regeneration of the working electrode is of primary importance but regeneration of the other electrodes may also be quite desirable; since the inventive method when practiced as disclosed herein has no detrimental effect regardless of which probe electrode is regenerated, a typical regeneration made e.g. in the course of normal EAP maintenance will involve all probe electrodes.

The probe electrodes may be regenerated one after the other or simultaneously. For optimum results current control may be required, notably in simultaneous regeneration of several probe electrodes; for individual or sequential probe electrode regeneration with the preferred current sources disclosed herein particular current control is not required when standard EAPs are regenerated.

Generally, the electrolyte-exposed surface of the probe electrodes consists of Ag, Au, a platinum group metal, an alloy of the mentioned metals or of a stainless steel, e.g. 316 grade or equivalent high grade alloys that are resistant to the normal operating conditions of the probe. For many types of probe use, the counter electrode preferably consists of silver or a conventional combination of silver and a silver compound, e.g. an Ag/AgCl combination.

As regards specific examples of electrolytes suitable for the inventive method the requirements of being "non-polluting" (reference is working electrode) and "non-aggressive" imply that the aqueous electrolyte should be substantially free of water-insoluble or water-immiscible constituents as well as of metal-dissolving, metal-reacting and metal-complexing constituents, such as zinc and any heavy metal cations and cyanide anions; further, the presence of organic surfactants is not normally preferred. A resistivity in the range from about 10 to about 10,000 Ohm·cm is typical for the electrolyte.

A first group of electrolytes preferred for the inventive regeneration method includes those aqueous electrolytes that are normally used in the EAP or MEAC for normal electroanalytical operation, i.e. when the electrolyte within the cell is covered by the semipermeable membrane; it will be understood in this context that the membrane will not be mounted when the EAP is subjected to the inventive regeneration.

For example, the electrolyte for regeneration may include cations selected from alkali metals, alkaline earth metals and ammonium, while suitable anions can be selected from hydroxides, carbonates, bicarbonates, phosphates and halides; sulphates and nitrates are suitable but less preferred. Cations of metals that are capable of forming intermetallic compounds or solid solutions with the noble metal of the working electrode, such as zinc and heavy metals, should be avoided in the electrolyte.

Typical concentrations of any given anion or cation are generally below about 2 M and a total concentration of dissolved electrolyte of not substantially above 20%, by weight of the electrolyte, is preferred. When using strongly alkaline electrolyte components, such as alkali metal hydroxides, concentrations should be sufficiently low to preclude damage to cell components; acid salts and acids, e.g. hydrohalide acids, may be used under the same precaution but are less preferred for typical regeneration. Buffered electrolytes may be used but are not normally required. More specific examples will be given in the working examples.

While not wishing to be bound by any specific theory, it can be assumed that the beneficial results obtainable by the inventive regeneration method using the effects of relatively high current densities in the presence of electrolyte are based in part, at least, upon the effects of incipient gas formation at the working electrode. Investigations into the phenomena occurring at the electrode/electrolyte interface during electrolytic metal deposition indicate that the generation of hydrogen or oxygen at a respective electrode during electrolysis of water from the electrolyte is generally accompanied by a supersaturation of the electrolyte near the electrode so that each nucleation that leads to formation of a gas bubble causes a minute pressure shock, probably at velocities in the sonic range; gas evolution at the electrodes upon electrolytical decomposition of water may thus be envisaged as being accompanied by a multiplicity of sonic shocks at or near the electrode surface.

It is assumed, however, that gas formation and any secondary consequences thereof are not the only cause of the remarkable regeneration effects of the inventive method and direct reactions including reductive or oxidative changes may be involved.

It is to be noted in this context that so-called electrolytical degreasing methods have been in use for about a century, and that electroanalytical probes of the MEAC type have been in use since two and half decades; yet, electrolytical cleaning has never been disclosed, to the best of patentee's knowledge, for treatment of MEACs.

In a similar vein, removal of metal coatings by electrolytical means is a conventional step, e.g. in gravimetric analysis involving electrolytical deposition of a metal of interest upon a platinum electrode; since such electrodes are reused many times, removal of metallic deposits by reversing the polarity of the platinum electrode and increasing the current for rapid removal has been a conventional step yet does not seem to have precipitated the teaching that a comparable method could be of use for regeneration of MEACs and similar probes. It will be observed in this context that a "reversal of polarity" may, but need not, be involved in the inventive regeneration method, e.g. that a probe electrode that is the cathode (anode) in normal analytical probes will be the anode (cathode) in the regeneration method, i.e. vis-a-vis the external or regeneration electrode.

The general and critical parameter is the increased current density in the presence of the aqueous electrolyte; polarity may be reversed but non-reversal may be preferred for a number of important embodiments, notably regeneration of the (normally cathodic) working electrode of oxygen sensors and of the working electrode of (normally anodic) hydrogen sensors. Non-noble metals should be made cathodic.

Direct current is preferred but a pulsing DC is suitable as well and periodic or aperiodic reversal of polarity may be of use for special purposes. A typical and preferred current source for carrying out the inventive method, notably under field conditions, is an optionally rechargeable 3 to 4.5 V battery of the type used for flash-lights and similar purposes if its capacity is sufficient to supply the current densities required for regeneration and a voltage sufficient for electrolytical decomposition of water, i.e. at least about 1.2 V.

Generally, the regenerator electrode external to the MEAC or similar EAP should be made of an electrically conductive material that will not produce or introduce contaminants when used under operating conditions of the inventive method; noble metals of the type suitable for the working electrode are generally suitable for the regenerator electrode, at least in those portions thereof that are in electrolytical contact with the aqueous electrolyte.

However, for reasons of costs, less valuable electrode materials can be used for the regenerator electrode and electrically conductive carbon, e.g. in the form of graphite, is a preferred material for the external regenerator electrode here.

While any suitable arrangement of the external electrode and the aqueous regeneration electrolyte for carrying out the inventive method can be used, e.g. a cup, flask or similar enclosure means for the regenerator electrolyte and the regeneration electrode, it is greatly preferred according to the invention to use an enclosure means with two open ends, e.g. a tubular structure or sleeve, that is capable of being sealingly closed at one end by the electroanalytical probe that is to be regenerated.

The advantage of a regenerating device embodying such a structure is that a very small amount of regeneration electrolyte will normally be sufficient for regeneration of a probe and that, as a rule, the regeneration electrolyte will automatically be discarded after regeneration so as to preclude recontamination effects.

Accordingly, the invention includes, as a general structural embodiment, a novel regenerator for electroanalytical probes having an enclosure or sleeve formed by a hollow and preferably tubular structure made of an inert insulator and having two ends; the lower end of the sleeve will be closed and sealed by the sensing end of the probe that is to undergo regeneration; the regenerator includes an electrode, e.g. made of graphite, situated for contact with an electrolyte that is introduced into the sleeve after the lower end thereof is closed by the probe. Preferably, the regenerator electrode has a predetermined surface exposed to the regenerator electrolyte, said surface being at least about 100 times greater than the exposed surface of the working electrode of the probe that is being regenerated.

Then, one end of a current source is connected with the regenerator electrode while the other is connected with at least one electrode of the probe.

With a simple DC current source, such as a standard 3 V battery, the regenerator thus mounted will be capable to cause a current density of 50 to 800 mA/cm$^2$ at the probe electrodes. After a period of from typically 30 seconds to 60 minutes the probe is regenerated as evidenced by the quick response and lack of current noise which is characteristic for a new probe in "virgin" condition.

BRIEF DESCRIPTION OF THE DRAWINGS

The invention will be better understood and objects other than those set forth above will become apparent when consideration is given to the following detailed description. Such description makes reference to the annexed drawings which illustrate the diagram of a prior art MEAC with a guard electrode for purposes of comparison with the invention as well as exemplary embodiments of the invention and wherein FIG. 1A is a diagrammatic cross-sectional view of a regenerator device according to the invention;

FIG. 1B is an enlarged representation of the regenerator of FIG. 1A shown with an electroanalytical probe in position for regeneration; and FIG. 1C is a diagrammatic top view of FIG. 1A.

DETAILED DESCRIPTION OF THE PREFERRED EMBODIMENTS

The regenerator 1 shown in all Figures is formed by an enclosure or sleeve 10 having a tubular body portion 11 made of a structural plastic such as a polyacetal (e.g. DELRIN, reg. trademark), a Teflon-type fluorocarbon, a polyamide or the like cell insulator material of the type disclosed in U.S. Pat. No. 4,096,047 for MEACs.

The lower end 101 of body 11 is dimensioned to receive the sensing end of an EAP as explained below; a sealing means 13 is formed for engagement with the end portion of the EAP and comprises an annular recess 131 that holds an O-ring 132 or the like sealing member. The upper end 102 of the enclosure or sleeve 10 is formed by an annular mounting member or ring 111 connected with body 11 by a thread 113 or the like connection. A passage 112 is provided in ring 111 for a lead wire 151, e.g. of platinum, that provides for an electrical connection of regenerator electrode 15 with the first outlet end or terminal 191 of an electrical source 19 via connection 193.

The regenerator electrode 15 is an annular structure made of graphite inserted into recess 114 and securely held in tubular body or body portion 11 by ring 111. The end face 103 or similar end portion or shoulder serves as a stop means for positioning a probe 12 as explained below.

The overall sleeve-type structure of the preferred regenerator 1 is further apparent from the top view shown in FIG. 1C.

FIG. 1B shows the regenerator 1 of FIGS. 1A and 1C in an enlarged presentation with the sensing end or probe 12 of a conventional MEAC as probe 12 including an optional guard electrode 18 in addition to a working electrode 14 and counter electrode 16, depicted in a diagrammatic representation.

A shoulder 123 or the like edge of the sensing end probe 12 acts as a second stop means to cooperate with the first stop means 103 at the lower end 101 of regenerator 1 so that the sensing face 121 (membrane removed prior to insertion) extends into the electrolyte receiving space 105 formed within regenerator 1 in the vicinity of the regenerator electrode 15.

The sensing end or probe 12 comprises the working or sensing electrode 14 having an exposed circular surface 140 made of Au or Pt. Electrode 14 is enclosed by an insulator 142 and is electrically connected with a lead or connector 141. The guard electrode 18 having an exposed surface 180 extends around the sensing electrode 14 in a concentric manner and has a connector 181 at the outlet end of probe 12.

Another insulator layer 162 is arranged between guard electrode 18 and counter electrode 16 having an exposed surface 160 and a connector 161 at the outlet of probe 12. The housing 122 of probe 12 normally consists of an insulator material and extends into a cylindrical end portion 124.

For use of the regenerator 1 according to the invention an electrolyte 17, e.g. an aqueous 1N KOH solution, is filled via upper end 102 into space 105 to contact the entire sensing face 121 of probe 12 including the surface of electrodes 14, 16, 18 and a major portion of surface 150 of regenerator electrode 15.

Next, the second outlet end or terminal 192 of DC source 19 will be connected via a connection 194 with at least one probe electrode 14, 16, 18, e.g. by a distributor or switch 195 serving to connect source 19 alternatively as shown (or simultaneously with appropriate current control if desired) with the connector ends 141, 161, 181 of the probe electrodes by appropriate lines 196, 197, 198.

After a suitable period of regeneration of the probe electrodes, e.g. 15 seconds to 15 minutes per electrode, electrolyte 17 will be poured out through end 102 and switch 195 is moved in non-connecting position; flushing of regenerator 1 and probe 12 with electrolyte and/or water in connected position is optional. Switch 195 may be automated for providing predetermined regeneration periods of the probe electrodes.

Then, probe 12 is withdrawn from regenerator 1 and is ready for use after receiving the required electrolyte and membrane in conventional manner, e.g. as disclosed in EP No. 0 043 611. Specific examples of such regeneration operations will be given below; general parameters of the examples are as follows:

The criterion for the effect of the inventive probe regeneration used in the examples is the "response time" applied as a standard test; it is to be noted, however, that other advantageous effects including reduction or substantial elimination of output or terminal current noise as well as substantially complete removal of various fouling effects incurred upon analytical probe operation in probe-contaminating environments etc. have been observed but are less amenable to quantified expression. Hence, response time is used as a summary criterion for overall probe performance here.

The response time test is a standard method for testing probes that leave the factory in "virgin" condition. Generally, a response time of 10 minutes or less is regarded as indicating acceptable operation of a new probe when fitted with a 25 μm thick perfluoro alkoxy membrane (PFA); the test includes an "oxygen concentration step" (exposure to air or air-saturated water, on the one hand, and submersion in a medium known to be free of elemental oxygen) and measurement of the time from the application of the concentration step to the moment when the instrument for electroanalytical operation indicates a value of 1 ppb (per billion, $10^9$). The oxygen levels in the particular test correspond to 8 ppm (per million) before and zero ppb (per billion) after the step.

EXAMPLE 1

A used MEAC as probe 12 exhibiting a response time of 21 minutes was regenerated in the device shown in FIG. 1A using 3 ml of a standard electrolyte (56 g KOH and 74 g KCl per liter of water) for electroanalytical operation. Regenerator electrode 15 was connected with the positive output of a 3 V DC power supply. Probe electrodes 14, 16, 18 were connected successively, each for 30 seconds, with the negative output or terminal of the DC supply. Probe 12 was withdrawn from regenerator 1, washed with tap water, filled with the standard electrolyte and provided with a standard 25 μm perfluoroalkoxy (PFA).

In the standard test the regenerated probe exhibited a response time of less than 5 minutes. All values measured were taken at room temperauure (20°-25° C.). The MEAC was an oxygen sensor, Model 2110, Orbisphere Laboratories (Inc.), Geneva, Switzerland.

EXAMPLES 2 TO 5

The method of example 1 was repeated; response times before and after regeneration wer recorded and various electrolytes were used; the details are summarized in the following table:

| Example | Response time of probe 12 in minutes before and after regeneration | | Electrolyte (g per liter of water) |
|---|---|---|---|
| | before | after | Substance |
| 2 | 18 | 4 | 112; KOH |
| 3 | 16 | 5 | 100; Na$_2$HPO$_3$ |
| 4 )* | 19 | 6 | 56; KOH |
| | | | 74; KCl |
| | | | 20; K$_3$PO$_4$ |
| 5 )** | 12 | 6 | 56; KOH |

Notes:
)* intermediate rinsing omitted to simulate "accident" in regeneration operation
)** regeneration time of anode 16 extended to 90 minutes to simulate other "accident" in regeneration operation.

Various modifications of the above discussed embodiments of the invention will be apparent; for example, automated control devices may be used to select and/or control the regeneration current and/or the time during which the regeneration current is applied to any given probe electrode.

while preferred embodiments of the present invention were shown and described above it is to be understood that the invention is not limited to such embodiments but may be embodied and practiced within the scope of the following claims.

What is claimed is:

1. A method of regenerating an amperometric cell comprising at least two probe electrodes including at least one working electrode and at least one counter electrode, each of said electrode having an exposed surface for contact with a cell electrolyte provided within a cell space bounded by a membrane; said amperometric cell having, during electroanalysis, an operative current range limited by a maximum current density at said at least one working electrode; said method comprising the steps of: removing said membrane and said cell electrolyte from said amperometric cell and placing at least said at least two probe electrodes into contact with a regeneration electrolyte; placing a regenerator electrode into contact with said regeneration electrolyte; connecting said regenerator electrode and at least one of said at least two probe electrodes in circuit with a common electric power source and thereby subjecting said at least one of said at least two probe electrodes while in contact with said regeneration electrolyte, to a regeneration current at a current density which is substantially higher than said limited maximum current density in said amperometric cell during electroanaylsis; said higher current density being generated by said regeneration current at said at least one probe electrode and said regenerator electrode; maintaining said regeneration current at said higher current density at said at least one probe electrode; and thereafter removing said regeneration electrolyte from said at least two probe electrodes and refitting said membrane and said cell electrolyte to said amperometric cell.

2. The method of claim 1 wherein said at least one working electrode is subjected to said substantially higher current density.

3. The method of claim 2 wherein said at least one working electrode is subjected to said regeneration current at a current density in the range of from about 1 to about 1000 milliamperes per square centimeter of said exposed surface of said working electrode.

4. The method of claim 1 wherein said at least one counter electrode is subjected to said substantially higher current density.

5. The method of claim 1 wherein said probe electrode that is subjected to said substantially higher current density is a guard electrode of said probe.

6. The method of claim 5 wherein said exposed surface of said working electrode and of said guard electrode is made of a noble metal selected from the group consisting of gold, platinum group metals and alloys thereof.

7. The method of claim 1 wherein said operative current range is limited by a maximum current density of not above about 100 microamperes per square centimeter of said exposed surface of said working electrode.

8. The method of claim 1 wherein said counter electrode is selected from the group consisting of an elemental silver electrode and a combined elemental silver/silver compound electrode.

9. The method of claim 1 wherein said regenerator electrode is placed into contact with said regeneration electrolyte by means of a surface area which is at least about 100 times greater than a surface area by means of which said at least one working electrode is placed into contact with said regeneration electrolyte.

10. The method as defined in claim 1, further including the steps of:
subjecting said at least one probe electrode to said regeneration current for a time period which results in a substantially virgin condition of said at least one probe electrode as determined by the response time after refitting said membrane and said cell electrolyte to said amperometric cell.

11. A regeneration arrangement for regenerating an amperometric cell devoid of a membrane bounding a cell-electrolyte-filled space at a sensing end containing at least two electrodes including a working electrode and a counter electrode; said regeneration arrangement comprising: an enclosure means having a first open end and a second open end; said first open end of said enclosure means sealingly accommodating said sensing end of said amperometric cell; a regenerator electrode arranged within said enclosure means between said first open end and said second open end in an interior space for receiving a regeneration electrolyte for providing electrolytically conductive contact between said regenerator electrode and said at least two probe electrodes of said sensing end of said amperometric cell accommodated by said first open end of said enclosure means; and electrical connection means for connecting said regenerator electrode and said at least two probe electrodes in circuit with a common electric power source.

12. The arrangement of claim 11 wherein said enclosure means is a two-ended hollow body having an essentially tubular cavity comprising sealing means near said first open end; said regenerator electrode being arranged near said second open end.

13. The arrangement of claim 12 wherein said enclosure means consists of an essentially inert and electrically non-conducting material; and said regenerator electrode consists essentially of graphite.

14. The arrangement of claim 11 wherein first stop means is provided at said first open end of said enclosure means; second stop means provided at said amperometric cell inserted into said first open end of said enclosure means; and said first stop means contacting said second stop means in a regeneration position of said sensing end accommodated in said first open end of said enclosure means.

15. The arrangement of claim 11 wherein said sensing end of said amperometric cell is of a substantially cylindrical shape.

16. The arrangement of claim 11 further comprising switch means connected in circuit with said electrical connection means connected with said at least two probe electrodes, for connecting selected ones of said at least two probe electrodes to said common electric power source.

17. In the method of regenerating an amperometric cell devoid of a membrane bounding a cell electrolyte-filled space at a sensing end having at least two probe electrodes including a working electrode which is operated at a limited maximum current density during electroanalysis, and a counter electrode; the improvement comprising the steps of: providing a regenerator electrode and a regeneration electrolyte which are external to said amperometric cell to be regenerated; placing at least said at least two probe electrodes into contact with said regeneration electrolyte; placing said regenerator electrode into contact with said regeneration electrolyte; connecting said regenerator electrode and at least one of said at least two probe electrodes in circuit with a common electric power source and thereby subjecting said at least one of said at least two probe electrodes while in contact with said regeneration electrolyte, to a regeneration current at a current density that is substantially higher than said limited maximum current density during electroanalysis; said higher current density of said regeneration current being generated at said at least one probe electrode, and said regenerator electrode.

18. A regeneration device for regenerating an amperometric cell having a sensing end which contains at least two probe electrodes including at least one working electrode and at least one counter electrode, said regenerating device comprising:
an enclosure means having a first open end and a second open end;
said first open end being adapted to sealingly receive the sensing end of the amperometric cell in a regeneration position in said enclosure means;
said enclosure means defining an electrolyte space for receiving and holding a regeneration electrolyte;
a regenerator electrode arranged within said enclosure means between said first and said second open ends and in said electrolyte space for providing electrolytically conductive contact between said regenerator electrode and said at least two probe electrodes; and
electrical connection means for connecting said regenerator electrode and said at least two probe electrodes in circuit with a common electric power source.

19. The device of claim 18, wherein:
said enclosure means constitute a generally tubular body comprising sealing means near said first open end.

20. The device of claim 18, further including:

first stop means provided at said first open end of said enclosure means for cooperation with second stop means at said amperometric cell for locating said sensing end of said amperometric cell in said regeneration position in said enclosure means.

21. The device of claim 19, wherein:
said enclosure means consists essentially of a substantially inert and electrically non-conducting material; and
said regenerator electrode consists essentially of graphite.

22. The device of claim 18, wherein:
said enclosure means has a substantially cylindrical configuration for receiving a substantially cylindrical sensing end of said amperometric cell.

23. The device of claim 18, further including:
switch means for connecting said common electric power source with selected ones of said at least two probe electrodes.

24. The device as defined in claim 18, wherein:
said regenerator electrode constitutes an annular electrode.

25. The device as defined in claim 24, wherein:
said enclosure means comprises a generally tubular body, a first portion of said tubular body carrying sealing means for engaging an amperometric cell to be regenerated, and defining a first open end;
a second portion of said tubular body threadably connected to said first portion and defining a second open end;
a shoulder formed in the interior surface of said first tubular body for receiving said annular regenerator electrode; and
said annular regenerator electrode being held between said second portion and said shoulder formed in said first portion of said tubular body in confronting relation to said electrolyte space for receiving said regeneration electrolyte.

26. The device as defined in claim 18, further including:
switch means connected with said common electric power source for connection to the at least two probe electrodes of said amperometric cell to be regenerated.

* * * * *